United States Patent [19]

Dubut

[11] Patent Number: 5,042,492

[45] Date of Patent: Aug. 27, 1991

[54] PROBE PROVIDED WITH A CONCAVE ARRANGEMENT OF PIEZOELECTRIC ELEMENTS FOR ULTRASOUND APPARATUS

[75] Inventor: Patrick Dubut, Tourrettes S/Loup, France

[73] Assignee: General Electric CGR SA, Issy les Moulineaux, France

[21] Appl. No.: 368,337

[22] PCT Filed: Nov. 24, 1987

[86] PCT No.: PCT/FR87/00466

§ 371 Date: May 23, 1989

§ 102(e) Date: May 23, 1989

[87] PCT Pub. No.: WO88/04089

PCT Pub. Date: Jun. 2, 1988

[30] Foreign Application Priority Data

Nov. 28, 1986 [FR] France ................................ 86 16664

[51] Int. Cl.[5] ................................................ A61B 8/00

[52] U.S. Cl. ................................ 128/662.03; 310/371

[58] Field of Search ....................... 128/662.03, 661.10; 310/336, 369, 371

[56] References Cited

U.S. PATENT DOCUMENTS 4,205,686 6/1980 Harris et al. ................... 128/662.03
4,208,602 6/1980 Stoller ............................. 310/369 X
4,217,684 8/1980 Brisken et al. ...................... 29/25.35
4,556,066 12/1985 Semrow ......................... 128/662.03
4,747,192 5/1988 Rokurota .......................... 29/25.35
4,894,895 1/1990 Rokurohta ........................ 29/25.35

OTHER PUBLICATIONS

Patent Abstracts of Japan, vol. 10, No. 113 (E-3999) (2170), Apr. 26, 1986, & JP. A. 60249500 (Yokokawa Medical System K.K.) Dec. 10, 1985.

Patent Abstracts of Japan, vol. 7, No. 27 (E-156) (1172) Feb. 3, 1983, & JP. A; 57181299 (Yokogawa Denki Seisakusho K.K.) Nov. 8, 1982.

Patent Abstracts of Japan, vol. 5, No. 176 (E-81) (848) Nov. 12, 1981, & JP. A; 56102191 (Kouden Seisakusho K.K.) Aug. 15, 1981.

Patent Abstracts of Japan, vol. 10, No. 27 (E-378) (2084) Feb. 4, 1986, & JP. A, 60185500 (Shimazu Seisakusho K.K.) Sep. 20, 1985.

*Primary Examiner*—Francis Jaworski
*Attorney, Agent, or Firm*—Oblon, Spivak, McClelland, Maier & Neustadt

[57] ABSTRACT

In order to make a probe having a concave attack face, a continuous acoustic transition blade (5) is used. Said blade is metallized (7) and is common contact with all the front metallizations (6) of the piezoelectric elements of the probe. The rear metallizations (8) of the elements terminate electrically and independently backwards of the probe. As a result, the electric connection of the piezoelectric elements is simplified. Said probe is usable in experiments with ultrsounds where good focusing is desired.

8 Claims, 2 Drawing Sheets

PROBE PROVIDED WITH A CONCAVE ARRANGEMENT OF PIEZOELECTRIC ELEMENTS FOR ULTRASOUND APPARATUS

BACKGROUND AND SUMMARY OF THE INVENTION

An object of the present invention is a probe, provided with a concave arrangement of piezoelectric elements, for an ultrasound apparatus. A probe of this type can be used, in particular, in the medical field in association with an echograph type of apparatus. Nonetheless, it can find application in other fields where ultrasound is used and where, for needs of focusing, it is preferred to use probes provided with piezoelectric elements distributed on a concave surface.

A probe for an ultrasound apparatus comprises, in principle, several piezoelectric transducer elements to convert electrical signals applied to the elements into mechanical excitations and vice versa. These piezoelectric elements are arranged in the head of the probe according to a matrix type distribution, most often with two dimensions, sometimes with one dimension, for example in a bar. The making of a probe of this type, in the face of the need to supply, electrically and independently, each of the elements is not a simple problem. A solution, in principle, consists in fixing, to a metallized, flexible support, a plate of a piezoelectric crystal, and in making cuts in this plate without excessively penetrating the support. In this way, the desired distribution of the elements is obtained. In having made sufficiently wide cuts and in curving the elastic support, a desired concave shape can be imposed on it. In doing so, the electrical supply of the two faces of the piezoelectric elements is not easily resolved. In effect, since the useful acoustic transmission is propagated on the side of the concavity, it is inappropriate to make independent connection circuits on this surface. This is all the more troublesome as, for reasons of acoustic propagation, it is necessary to place, on top of each of the elements, an acoustic transmission blade with a thickness substantially equal to a quarter of the wavelength of the wave, which goes through it at the working frequency of the probe. This problem of connection is a major brake on the development of probes, especially those for which the piezoelectric arrangement is two-dimensional.

The characteristics of a concave ultrasound probe are known from the Japanese abstract 57181299. The support 1 known from this document is thermodeformable and the acoustic transition blade is cut up by saw marks. The joining of elements 3 to a plate 4 is known from the Japanese abstract 60249500. This plate is not described as being an acoustic transition blade.

An object of the present invention is to overcome these drawbacks in observing that, for the applications sought, with a focusing imposed by the curvature of the arrangement of the elements, it is not troublesome for the tips of elements covered with their transition blade to touch one another in the concavity of the probe. In the invention, the idea was then had of reversing the problem and using a common transition blade, continuously metallized throughout its surface, and to which all the piezoelectric elements are fixed. The result thereof is that the electrical connection for the differentiation of all the elements can be done through the rear of the probe, where there was previously the support. These electrical connection circuits disturb the rear wave of the probe, which is of no importance. They do not hamper the useful operation of the probe. The concave arrangements of piezoelectric elements are obtained by using flexible blades which may possibly be thermodeformable. The metallizations of the front and rear faces enable the application of an electrical field parallel to the direction of propagation of the sound waves. This arrangement is advantageous because it improves the coupling coefficient between the electrical field and the acoustic field.

The piezoelectric elements comprise, for example, plastic elements such as $PVF_2$ or copolymer $PVT_2F$: a ceramic such as PZT for example, the polymer compound PZT or the $PBTiO_3$ or a crystal.

An object of the invention, therefore, is a probe for ultrasound apparatuses provided with a concave arrangement of piezoelectric elements, said elements being each covered, on their emitting face, in front of the concavity, with an acoustic transition blade, characterized in that adjacent blades form one and the same continuous integral blade covering several elements.

BRIEF DESCRIPTION OF THE DRAWINGS

The present invention will be better understood from the reading of the following description and the examination of the accompanying figures. They are given solely by way of indication and in no way restrict the scope of the invention. The figures show.

DETAILED DESCRIPTION OF THE PREFERRED EMBODIMENTS

Figure 1:
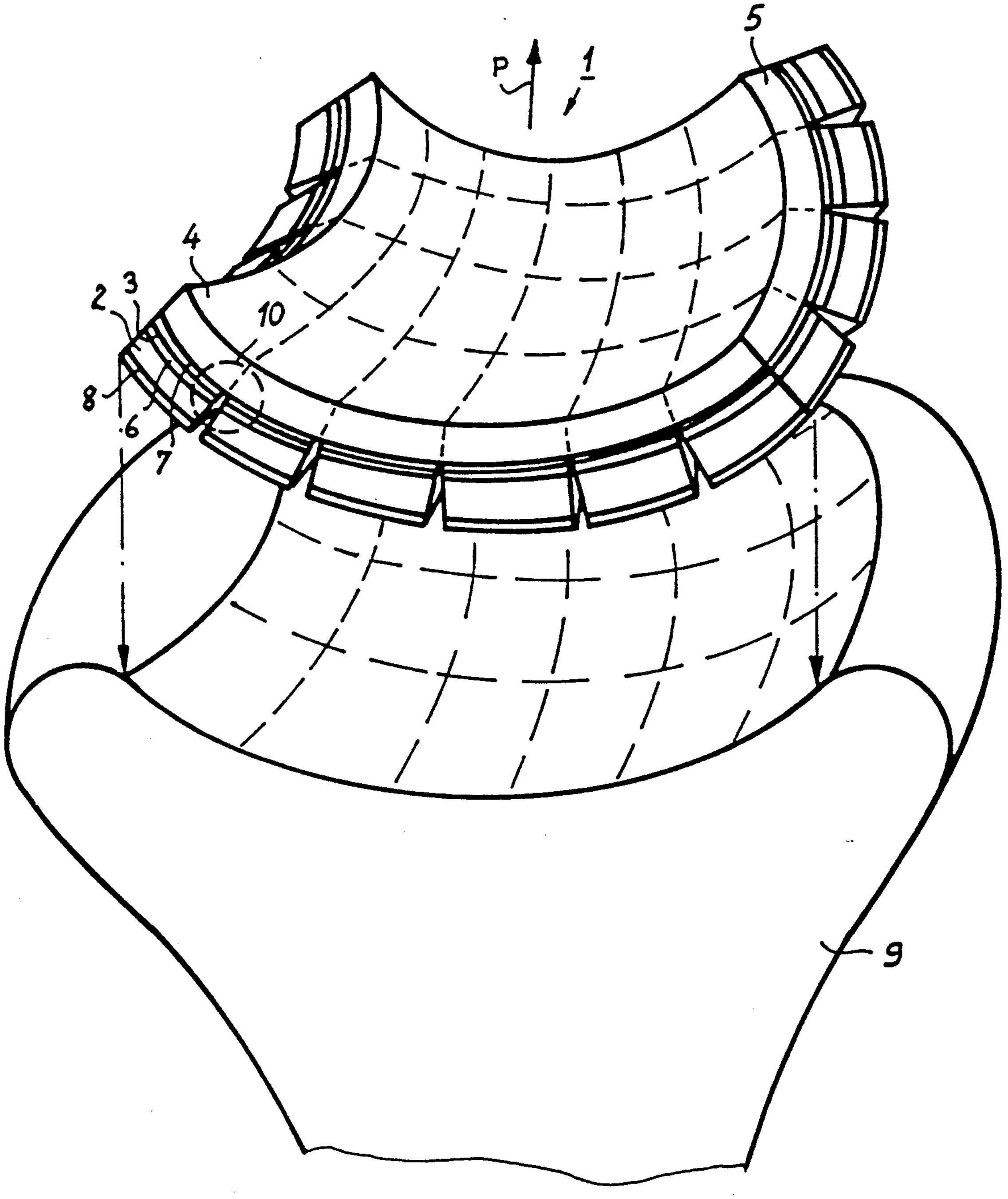
FIG. 1: a probe according to the invention.
Figure 2:
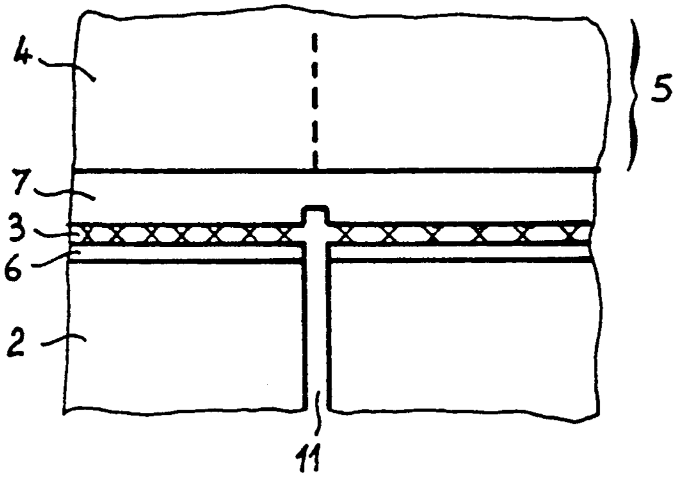
FIG. 2: a detail of an embodiment of the probe of FIG. 1 during its fabrication process.

FIG. 1 shows a probe according to the invention. This probe has a concave arrangement 1 of piezoelectric elements such as 2. The concavity is a concavity in two orthogonal dimensions. The surface is warped. It can, of course, be concave in one dimension and, in this case, the surface is cylindrical. The elements are each covered, on their face 3 in front of the concavity, with an acoustic transition blade. For example, for the element 2, its transition blade 4 is limited partly by dashes on the drawing. The characteristic feature of the probe of the invention lies in the fact that adjacent blades form one and the same continuous, integral blade 5 covering several elements, in general all the elements. To ensure the electrical connection with the electrodes 6 (obtained by metallization) of the piezoelectric elements, the blade 5 is provided, on its face in front of these elements with a metallization 7, which comes into contact with the metallizations of these elements. The other metallization 8 of the piezoelectric elements can be connected in a standard way. These connections can be incorporated in a base 9 which can be used, besides, to maintain and manipulate the probe. The presence of the differentiated electrical connections vertical to the metallizations 8 cannot cause disturbance in the acoustic signals emitted or received because they are located behind the probe with respect to the useful direction P of propagation. FIG. 2 shows a detail of an embodiment of the probe at a position referenced 10 in FIG. 1. During the fabrication of a probe, according to the invention, with a concave arrangement of elements, a plate of piezoelectric crystal metallized on both its faces is bonded to a blade 5 previously metallized with a layer 7. The metallization 7 of the blade is preferably thick: in one example, it is equal to between 15 and 20 micrometers. The metallization of the crystal is normal. It may have a far smaller thickness. The bonder used to fix the crystal to the blade is such that it enables electrical continuity at all places between the two metallizations. At this stage of manufacture, cuts 11 are made on the rear face of the crystal, with the object of separating, in the plate, the elements from one another. The cut 11 has the particular feature of being made with precaution. In a preferred way, its depth extends up to mid-thickness of the metallization 7 of the blade 5. It is possible, with tolerances of the order of 1 micrometer, to true the surfaces of the blade and the piezoelectric crystal. With a saw that is guided accurately with reference to the plane of the arrangement, it is then possible to see to it that the cut does not break the electrical link formed by the metallization 7.

Figure 3:
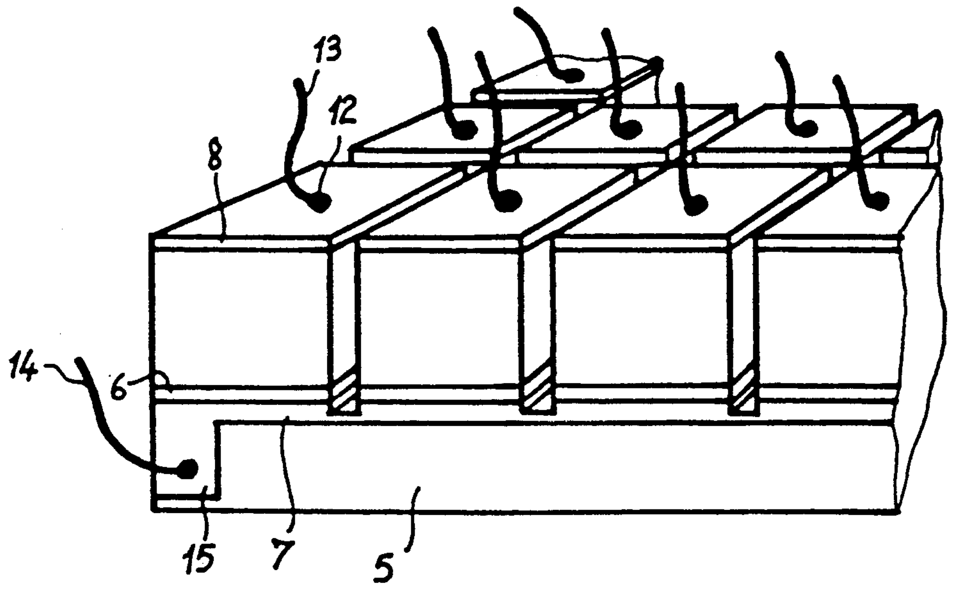
FIG. 3: a detail of an embodiment of the connection circuit of piezoelectric elements.

FIG. 3 shows how it is possible to achieve, in a simple way, the electrical connection to each metallization 8 made on the other face of an element. In a preferred way, a thermocompression technology is used. With this technology, the end 12 of the connecting wires 13 is pressed against the metallizations 8. In heating this end at the instant of this compression, a sufficient electrical connection is obtained. Similar action is taken with a wire 14 which ends on a peripheral part 15 of the metallization 7 of the blade 5.

At this stage of fabrication, the curvature of the arrangement is done. This arrangement may be concave with only one dimension or concave, as shown in FIG. 1, with two dimensions. To this end, the material forming the continuous blade is a deformable material. In a preferred embodiment, the material of the blade 5 is even a thermodeformable material. In one example, this blade is made of a cold polymerizable polyurethane. Under these conditions, it is enough to subject the blade/crystal set, thus formed and then cut, to a heating-/cooling cycle. During this cycle, under heat, the arrangement is subjected to forces tending to deform it in the desired way. To this end, it is possible to use an appropriate form to rest against the set. During the cooling, the set is hardened with the form that was imposed on it. After this operation, a base 9 is made for the arrangement by pouring, between the rear faces of the elements, a polymerizable synthetic element. The wires 13 or 14 emerge from this base. They are subsequently connected to the control circuits of the ultrasound apparatus used.

The materials forming the base are preferably chosen from among those likely to show a null acoustic impedance. In a preferred way, the contact between the elements and the base is not very intimate. The presence of an interposed thin film of air is even favourable to the lowering of the value of the rear acoustic impedance. This loose contact is made possible by the choice of a thermocompression bond as indicated: it is not necessary to bond a rigid printed circuit based connection device against the rear faces of the elements.

I claim:

1. A probe for an ultrasound apparatus comprising:

a concave arrangement of a plurality of separate piezoelectric elements, the piezoelectric elements each being covered, on an emitting face thereof at an inner side of the concave arrangement, with an acoustic transition blade, said acoustic transition blades comprising a continuous integral blade covering more than one emitting face of the piezoelectric elements, said continuous integral blade having a continuous metallization, on a face thereof juxtaposed to the piezoelectric elements, for electrically connection to metallizations provided on emitting faces of said piezoelectric elements adjacent said continuous blade, said metallization on said continuous integral blade having a thickness sufficient to permit said concave arrangement of the piezoelectric to have separations between each of the separate piezoelectric elements, each of the separations extending substantially up to an intermediate thickness of the metallization of said continuous integral blade.

2. A probe according to claim 1, wherein said continuous integral blade is made of a deformable material.

3. A probe according to claim 2, wherein said continuous integral blade is made of a thermodeformable material.

4. A probe according to claim 1, wherein said concave arrangement is two-dimensional.

5. A probe according to any of the claim 1, wherein said concave arrangement is a bar.

6. A probe according to claim 1, wherein said concavity is a two-dimensional concavity.

7. A probe according to claim 1, wherein said concavity is a one-dimensional concavity.

8. A probe according to claim 1 or 2, wherein each of said piezoelectrical elements are electrically connected by wires thermocompressed on a face of the elements opposite to the face juxtaposed to said continuous integral blade.

* * * * *